United States Patent
Bond et al.

(10) Patent No.: US 7,642,077 B2
(45) Date of Patent: Jan. 5, 2010

(54) BIOCOMPOSITE COMPRISING CO-PRECIPITATE OF ENZYME, SILICATE AND POLYAMINE

(75) Inventors: Risha Bond, Mountain View, CA (US); Michael C. Jewett, Copenhagen (DK); Joseph C. McAuliffe, Sunnyvale, CA (US); Donald E. Ward, II, San Carlos, CA (US)

(73) Assignee: Genencor International, Inc., Palo Alto, CA (US)

( * ) Notice: Subject to any disclaimer, the term of this patent is extended or adjusted under 35 U.S.C. 154(b) by 178 days.

(21) Appl. No.: 11/007,437

(22) Filed: Dec. 7, 2004

(65) Prior Publication Data
US 2005/0158837 A1 Jul. 21, 2005

Related U.S. Application Data

(60) Provisional application No. 60/528,241, filed on Dec. 8, 2003.

(51) Int. Cl.
C12N 11/14 (2006.01)
C12N 11/02 (2006.01)
C12N 11/04 (2006.01)
(52) U.S. Cl. .................. 435/176; 435/177; 435/182
(58) Field of Classification Search ............... None
See application file for complete search history.

(56) References Cited

U.S. PATENT DOCUMENTS

| | | | |
|---|---|---|---|
| 5,776,741 | A | 7/1998 | Pedersen et al. |
| 6,395,299 | B1 | 5/2002 | Babich et al. |
| 2004/0039179 | A1 | 2/2004 | McAuliffe et al. |
| 2005/0095690 | A1 | 5/2005 | Naik et al. |

FOREIGN PATENT DOCUMENTS

| | | |
|---|---|---|
| EP | 0676414 | 10/1999 |
| WO | WO 02/083741 | 10/2002 |
| WO | WO 03/099843 A2 | 12/2003 |

OTHER PUBLICATIONS

Maria M. Andersson, et al.; "Protein Stabilising Effect of Polyethyleneimine"; Journal of Biotechnology; V. 72 (1999) 21-31.
Thibaud Coradin, et al.; "Interactions of Amino-Containing Peptides with Sodium Silicate and Colloidal Silica: A Biomimetic Approach of Silicification"; Langmuir (2002), 18, 2331-2336.
I. Gill; "Bio-doped Nanocomposite Polymers; Sol-Gel Bioencapsulates"; Chem. Matter.; vol. 13, 3404-3421 (2001).
J.F. Kennedy; "Principles of Immobilization of Enzymes"; in Handbook of Enzyme Biotechnology (Ed. A. Wiseman; Ch. 4, p. 149 (1985).
N. Krogen, et al; J. Biol. Chem.; vol. 276, 26066 (2001).
G.M. Lindquist and R.A. Stratton; J. Colloid Interface Science; vol. 55 p. 45 (1976).
Heather R. Luckarift, et al.; "Enzyme Immobilization in a Biomimetic Silica Support"; Nature Biotechnology; vol. 22 No. 2; (Feb. 2004) 211-213.
T. Mizutani, et al.; Bull. Chem. Soc. Jpn.; vol. 71 p. 2017 (1998).
S.V. Patwardhan, et al.; "Effect of Process Parameters on the Polymer Mediated Synthesis of Silica at Neutral pH"; Silicon Chemistry; vol. 1, 47-55 (2002).
K. Shimizu and D. E. Morse; "The Biological and Biomimetic Synthesis of Silica and Other Polysiloxanes"; in Biomineralization (Ed E. Baeuerlein); Ch. 14, p. 207 (2000).
International Search Report PCT/US2004/41682, mailed Aug. 25, 2006.
Lindquist et al., The Role of Polyelectrolyte Charge Density and Molecular Weight on the Adsorption and Flocculation of Colloidal Silica with Polyethylenimine. Journal of Colloid and Interface Science; Apr. 1976, vol. 55, No. 1, pp. 45-59.
Mizutani et al., Silicic Acid Polymerization Catalyzed by Amines and Polyamines. Bull.Chem. Soc. Jpn. 1998, vol. 71, pp. 2017-2022.
Patwardhan et al., Effect of Process Parameters on the Polymer Mediated Synthesis of Silica at Neutral pH. Silicon Chemistry. 2002, vol. 1, pp. 47-55.
Kroger et al., Silica-Precipitating Peptides from Diatoms. The Journal of Biological Chemistry, Jul. 13, 2001, vol. 276, No. 28, pp. 26066-26070.
Coradin et al., Interactions of Amino-Containing Peptides with Sodium Silicate and Colloidal Silica: A Biomimetic Approach of Silicification. Langmuir. 2002, vol. 18, pp. 2331-2336.
Gill, I. Bio-Doped Nanocomposite Polymers: Sol-Gel Bioencapsulates. Chem. Mater. 2001, vol. 13, pp. 3404-3421.
Luckarift, et al.; "Enzyme immobilization in a biomimetic silica support"; Nature Biotechnology ; vol. 22 (2004) pp. 211-213.
Gill, Iqbal and Ballesteros, Antonio, "Bioencapsulation within synthetic polymers (Part I): sol-gel encapsulated biologicals," Tibtech 18, 282-296 (Jul. 2000).
Gill, Iqbal, "Bio-doped Nanocomposite Polymers: Sol-Gel Bioencapsulates," Chem. Mater. 13, No. 10, 3404-3421 (2001).
Kroger, et al., "Polycationic Peptides from Diatom Biosilica That Direct Silica Nanosphere Formation," Science 286, 1129-1132 (Nov. 5, 1999).

Primary Examiner—David M Naff
(74) Attorney, Agent, or Firm—Howrey LLP; Viola T. Kung

(57) ABSTRACT

This invention relates to a method of immobilizing biocatalysts including protein and cells by co-precipitation with silicate or organosilicate matrices through the action of an organic template molecule. The organic template molecule is in general a polyamine such as polyethylenimine (PEI), or polypeptide compound bearing at least two or three basic residues selected from the group consisting of lysine, arginine, histidine, proline, hydroxyproline, N-methylhistidine, ornithine, taurine, δ-hydroxylysine, and δ-hydroxy-ω-N,N,N trimethyllysine. The invention is also directed to a silica biocomposite comprising co-precipitates of active biocatalysts, silica or organosilicates, and an N-containing organic template molecule. Such silica biocomposites are useful in biocatalysis, and other applications requiring an immobilized biocatalyst. Preferred biocatalysts for this invention are enzymes and whole cells.

14 Claims, 2 Drawing Sheets

BIOCOMPOSITE COMPRISING CO-PRECIPITATE OF ENZYME, SILICATE AND POLYAMINE

This application claims priority to U.S. provisional application No. 60/528,241 filed Dec. 8, 2003. The content of which is incorporated herein by reference in its entirety.

FIELD OF THE INVENTION

This invention relates to a process for the immobilization of biocatalysts such as enzymes and cells by co-precipitation of biocatalysts with silicate or organosilicates through the action of an organic template molecule. The invention also relates to silica biocomposites containing silica, biocatalyst, and an organic template molecule. Such silica biocomposites are useful for biocatalysis, and other applications requiring an immobilized biocatalyst.

BACKGROUND OF THE INVENTION

Immobilized biocatalysts have found wide application in diverse areas including food processing, fine chemical production, biosensors, fuel cells and bioremediation. Immobilization of a biocatalyst, such as an enzyme, can confer a number of advantages relative to the free catalyst, including the ability to operate in organic solvents, recyclability and ease of removal from the process stream. Additional advantages include improvements in stability, favorable alterations in kinetic parameters and suitability for continuous production (Kennedy, "Principles of immobilization of enzymes" in *Handbook of Enzyme Biotechnology*, Ed. A. Wiseman, Ch 4, P.147 (1985)).

An immobilized biocatalyst refers to the combination of a biocatalyst and an insoluble support material. The nature of the association between the biocatalyst and the support material can be either covalent or non-covalent interaction. The biocatalyst can be attached to the surface of the support material, or distributed throughout the material in a homogenous fashion. The biocatalyst can also be physically entrapped within a porous gel matrix. The insoluble, or solid support may take the form of particles, powders, monoliths, gels, films, coatings and other materials. The solid support in general has a high surface area to maximize the contact of the immobilized biocatalyst with the reaction medium. Highly porous solid supports are preferred as they maximize surface area to volume of the immobilized biocatalyst.

Current methods for producing immobilized biocatalysts can be divided into 4 subcategories: (a) adsorption to a matrix such as carbon, chitin, celite and synthetic polymers, (b) crosslinking enzyme crystals and whole cells with gluteraldehyde and other agents, (c) gel entrapment in silica sol-gels, alginate and protein matrices, and (d) covalent attachment to resins and other carriers.

By immobilization, the performance of a biocatalyst is in general improved enough so as to offset the costs associated with the process or facilitate reaction conditions not possible without an immobilized biocatalyst, such as continuous processes. However, inexpensive immobilization methods often suffer from a number of drawbacks including lack of enzymatic and mechanical stability, leaching of the biocatalyst, fouling and limited catalytic efficiency. Other immobilization methods, such as silica sol-gel based procedures, require curing and drying steps that greatly increase production times (Gill, I. (2001) *Chem, Mater.* 13: 3404-3421).

There remains a need for a method to produce immobilized biocatalysts economically and to avoid many of the drawbacks associated with the current methods. The invention described herein provides for such methods and demonstrates the performance of the materials made thereby.

SUMMARY OF THE INVENTION

This invention is directed to a method of immobilizing biocatalysts such as enzymes and whole cells by co-precipitation of biocatalysts with silicate and/or organosilicate solution through the action of an organic template molecule. The method comprises the steps of: (a) mixing together a solution comprising one or more biocatalysts, a solution comprising an organic template molecule, and a silicate or an organosilicate solution, and (b) forming co-precipitates of biocatalysts, silica and an organic template molecule, wherein the biocatalyst retains catalytic activity. An organic template molecule, for example, is a polyamine, or a polypeptide bearing at least 2 basic amino acid residues.

In one embodiment of the invention, the silicate solution is prepared by neutralizing a dilute alkali metal silicate solution with an acid or an acidic resin to form a silicate solution. In another embodiment of the invention, the silicate solution is prepared by hydrolyzing a tetraalkylorthosilicate to form a silicate sol, then adding the silicate sol to a buffer to form a silicate solution.

The invention is also directed to a silica biocomposite comprising co-precipitates of immobilized biocatalyst(s), silica or organosilicates, and an organic template molecule; wherein the immobilized biocatalyst is catalytically active. The biocomposite can be collidal or solid. The biocomposite is an amorphous composite of aggregated nanoparticles and does not partition into layers. Such silica biocomposites are useful in biocatalysis, and other applications requiring an immobilized biocatalyst.

DETAILED DESCRIPTION OF THE INVENTION

Figure 1:
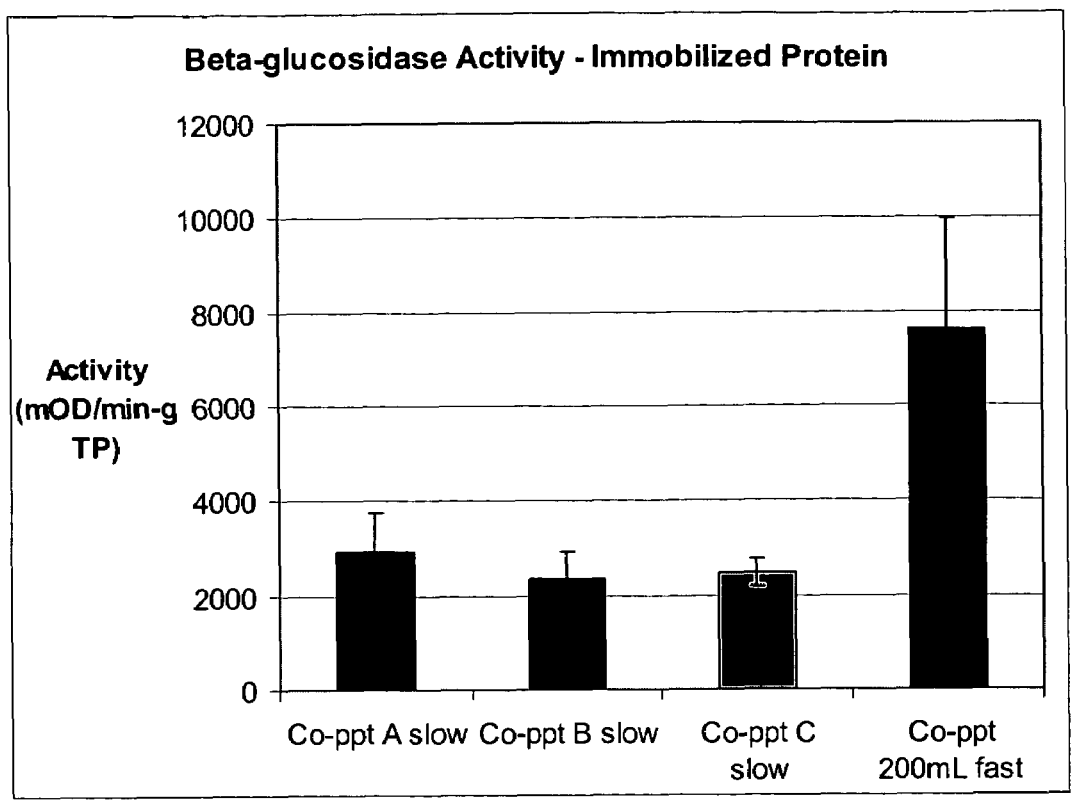
FIG. 1 depicts the β-glucosidase activity in the silica biocomposite prepared by slow or fast co-precipitation.

This invention provides an efficient and rapid method for the immobilization of biocatalysts. The mode of immobilization involves the simultaneous co-precipitation of one or more biocatalysts and an insoluble silicate or organosilicate from solution through the action of an organic template molecule. The immediate products of the resulting silica biocomposites are colloidal in nature, and can be isolated as a solid form. Such silica biocomposites contain the catalytically active biocatalysts and are useful in a variety of applications that require an immobilized biocatalyst.

For the purposes of this invention, a biocatalyst is defined as a material partly or wholly of biological origin that possesses catalytic activity. Such materials are typically proteins or protein containing materials with enzymatic activity, although certain classes of nucleic acids and carbohydrates can also have catalytic activity. Whole cells or parts thereof also represent biocatalysts for the purposes of this invention. These cells might be of either prokaryotic or eukaryotic origin, including but not limited to bacterial, yeast and fungal organisms. A biocatalyst can be obtained from a variety of sources including microbiological, plant or animal origin and can take the form of a solution or a solid material of various states of purity, including but not limited to bacterial, yeast and fungal organisms.

Enzymes suitable for this invention can be any enzymes. Enzymes include but are not limited to commercially available types, improved types, recombinant types, wild types, variants not found in nature, and mixtures thereof. Suitable enzymes include hydrolases, cutinases, oxidases, transferases, reductases, hemicellulases, esterases, isomerases, pectinases, lactases, peroxidases, laccases, pectinases, catalases, nitrilases and mixtures thereof. Hydrolases hydrolyze substrates and include, but are not limited to, proteases (bacterial, fungal, acid, neutral or alkaline), amylases (alpha or beta), lipases, phospholipases, esterases, mannanases, cellulases, and mixtures thereof. Particular enzymes of interest are proteases, lipases, glycosidases, oxidoreductases, oxidases, ketoisomerases or esterases. An example of proteases is a subtilisin, produced by Bacillus species. Examples of lipases are cutinase *Candida antarctica* lipases A and B, and LIPOMAX™ lipase. Examples of glycosidases are β-glucosidase, lactase, and cellulase; particularly cellulase or cellulase components isolated from Trichoderma reesei, such as found in the product Clazinase. Examples of ketoisomerases are xylose isomerse and glucose isomerase. An example of an esterase is acyltransferase. An example of an oxidoreductase is laccase. An example of an oxidase is glucose oxidase. Suitable enzymes for this invention also include those sold by Genencor International, Inc. under the trade names PURAFECT™, PURASTAR™, PROPERASE™, PURADAX™, CLARASE™, MULTIFECT™, MAXACAL™, MAXAPEM™, and MAXAMYL™ (U.S. Pat. No. 4,760,025 and WO 91/06637); and those sold by Novo Industries A/S (Denmark) under the trade names ALCALASE™, SAVINASE™, PRIMASE™, DURAZYME™, DURAMYL™, LIPOLASE™, and TERMAMYL™. Amylases such as alpha amylases obtained from Bacillus licheniformis are also suitable enzymes.

In one embodiment of the present invention proteases and other enzymes are produced by aerobic fermentation of bacteria or fungi. These enzymes are generally secreted as extracellular proteins, but in some cases, enzymes can be isolated from the cell membrane or from within the cell by chemical, enzymatic or physical disruption. Commercially, the cells and cell debris are removed by processes such as centrifugation or filtration through porous media, often with the aid of flocculation agents.

An organic template molecule useful for this invention is an organic molecule that can promote the polymerization of silicates or organosilanes through the condensation of either silanol (Si—OH) or silanoate (Si—O$^{31}$) functionalities to form siloxane bonds (Si—O—Si). This template directed formation of siloxane bonds ultimately results in the precipitation of silicate and organosilicate network solids from solution. These reactions are shown in equations 1 and 2.

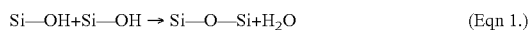

Si—OH+Si—OH → Si—O—Si+H$_2$O    (Eqn 1.)

Si—O$^-$+Si—OH → Si—O—Si+OH$^-$    (Eqn 2.)

In one embodiment of the invention, the organic template molecules are those that contain polar functionality that i) are able to form ionic or hydrogen bonds with silicate or organosilanes and ii) promote the polycondensation of silicates and organosilanes bearing silanol or silanoate groups to form siloxane bonds. Polar functionalities are defined as those containing heteroatoms such as nitrogen, oxygen, phosphorous and sulfur and include, but are not limited to amine, amide, amidine, guanidine, urea, carbamate, alcohol, alkoxide, ether, carboxylic acid, ester, phosphate, phosphine, thiol, and thiolate functional groups.

Preferred organic template molecules are those that comprise nitrogen (N)-containing polar functionality. Especially preferred organic template molecules are those containing one or more basic nitrogen atoms such as those containing primary, secondary, tertiary and quaternary amine functionality, in addition to amidine and guanidine functionality.

Organic template molecules useful for this invention are organic molecules such as polymers that contain nitrogen, carbon, hydrogen and oxygen, preferably containing two or more basic nitrogen atoms. Preferred organic template molecules of this invention refer to molecules where the basic nitrogen atoms are partially protonated at about pH 7, preferably at about pH 8, and more preferably at about pH 9 in an aqueous solution. The template molecules of this invention also include molecules containing quaternized nitrogen with a permanent cationic charge.

Examples of organic template molecules include polypeptides, polyamines, modified polypeptides, and modified polyamines. Polypeptides include those containing at least 2, preferably 3, basic amino acid residues selected from the group consisting of lysine, arginine, histidine, proline, hydroxyproline, N-methylhistidine, ornithine, taurine, δ-hydroxylysine, and δ-hydroxy-ω-N,N,N trimethyllysine. For example, a suitable polypeptide template molecule for the present invention is the R5 silaffin peptide, which has a sequence of SSKKSGSYSGSKGSKRRIL (S=serine; K=lysine; G=glycine; Y=tyrosine; R=arginine; I=isoleucine; L=leucine, SEQ ID NO:1)) and represents the backbone sequence of the naturally occurring silaffin-1A$_1$ peptide (Kroger et al., *Science,* 286: 1129-1132 (1999)). Suitable polypeptide templates also include those polybasic peptides that contain at least two basic amino acids as described in U.S. Patent Publication Application 2004-0039179.

Additional polypeptide template molecules include polylysine and polyarginine homooligomers such as short oligomers of poly-L-lysine and poly-L-arginine bearing between 3 and 20 amino acid residues.

Polyamines useful for the invention include linear or branched polyethylenimine, linear or branched polypropylenimine, polyallylamine and polyvinylamine. Other low molecular weight polyamines such as spermidine, spermine, triethylenetetramine, polypropylenimine dendrimers, and bis (2-ethylamino)-1,3-propanediamine are also useful. Amines can be primary, secondary, tertiary, or quaternary amines.

Polypeptide or polyamines can also be modified with hydrophobic functionalities including fluorescent dyes, fatty acids and sterols including cholesterol. For example modified polyamines for the present invention include cholesterol-modified polyamines such as those described by Geall, et al. (*Bioconjug Chem.,* 11:314-26 (2000)). Modified polyamines or modified polypeptides include fluorophore-modified polyamines or polypeptides. For example, a suitable template molecule is an arginine oligomer bearing 9 arginine residues and one aminohexanoic acid residue at the N-terminus labeled with the dye fluorescein (fluorescein-Ahx-R9, which has a sequence of Fluorescein-Ahx-RRRRRRRRR, Ahx=6-aminohexanoic acid; R=arginine, SEQ ID NO:2, SynPep Corp., CA).

Additional organic template molecules useful for this invention include polycationic flocculants such as those sold under trade names including SUPERFLOC™ (Cytec Industries, N.J.) and MAGNIFLOC™ (Ciba Specialty Chemicals, U.K.). Such flocculating agents are typically polymers of high molecular weight (>10 kDa) and are also referred to as polyelectrolytes due to the presence of multiple charges on the polymer molecules.

Zwitterionic molecules that bear both positive charges and negative charges can also be used as template molecules providing that the zwitterionic molecule bears 2 or more nitrogen functionalities. Examples of zwitterionic molecules useful as templates include some proteins with an isoelectric point (pI) above 9.

The silicate or organosilicate solution is prepared from silica precursors. For the purposes of the invention, a silicate precursor is an organic or inorganic substance that can give rise to silicon dioxide ($SiO_2$, silica) under selected conditions.

A silicate solution is a solution containing soluble silicon dioxide in the form of silicate or oligosilicate salts. The silicate solution used in the method is prepared by mixing a dilute alkali metal silicate solution or alkyl siliconate salt solution with an aqueous solution or an acidic resin to reduce the pH to 12 or lower to form a buffered silicate solution, such as a phosphate-buffered solution. The aqueous solution that reduces the pH of the alkali metal silicates or alkyl siliconate salts to 12 or lower, can be an acid, an acidic solution, or a low pH buffer. Acids useful for neutralization include phosphoric acid, citric acid, acetic acid, hydrochloric acid and the like. Weak acids such as phosphoric acid, citric acid, and acetic acid are preferred and phosphoric acid is more preferred. Acid resins useful for neutralization include Amberlite™ IR-120+, which is a strongly acidic cation exchanger, (Aldrich, Wis.).

Silicate precursors useful for the present invention include alkali metal silicates and alkyl siliconate salts. Alkali metal silicates include sodium silicates (e.g. sodium metasilicate, sodium orthosilicate and sodium silicate solutions), potassium silicates, and cesium silicates. Preferred alkali metal silicates are sodium silicates and potassium silicates. The most preferred alkali metal silicates are sodium silicates. Sodium silicates are commercially available. For example, sodium metasilicate and sodium orthosilicate can be obtained from Gelest Inc. (Morrisville, Pa.). Sodium silicate solution (a solution of SiO and NaOH) can be obtained from Sigma Aldrich.

Alkyl siliconate salts include sodium alkyl siliconate, potassium alkyl siliconate, and cesium alkyl siliconate. Preferred alkyl siliconate salts are sodium alkyl siliconate and potassium alkyl siliconate. The most preferred alkyl siliconate salt is sodium methyl siliconate. In this embodiment, the Si—OH groups capable of condensation with gel formation are generated by the protonation of Si—O-metal groups, such as an alkyl siliconate, e.g. sodium methylsiliconate, $MeSi(ONa)_3$.

Alternatively, the silicate solution is prepared by first hydrolyzing tetraalkylorthosilicate with an acid, a base, or a catalyst, to form silicate sols. Silicate sols are defined as a stable colloidal solution of silicate oligomers where the particle size is in the nanometer range. Silicate sols can undergo gelation or precipitation when exposed to a change in pH or a catalyst (Iler, R. K. '*The Chemistry of Silica*' (Wiley, 1979); Brinker, C. J. and Scherer, G. W. '*Sol Gel Science: The Physics and Chemistry of Sol-Gel Processing*' (Academic press, 1990)). Silicate sols are then added to a buffer, an acid or a base to form a silicate solution having a pH of about 2 to about 12, more preferably about 4 to about 10 and most preferably about 5 to about 9. Examples of tetraalkylorthosilicates include tetramethylorthosilicate (TMOS) and tetraethylorthosilicate (TEOS).

An organosilicate solution is a solution containing soluble silicon dioxide in the form of silicate or oligosilicate salts and an organosilane, a silane containing at least one silicon-carbon (Si—C) bond. The organosilicate solution used in the method is prepared by first hydrolyzing a tetraalkylorthosilicate and one or more organosilanes selected from the group consisting of alkyltrialkoxysilane, aryltrialkoxysilane, dialkyldialkoxysilane, and diaryldialkoxysilane, to form sols at either an acidic pH (pH 1-6) or a basic pH (pH 8-13). A preferred acidic pH is, for example, pH 1-5, or pH 1.5-4. A preferred basic pH is, for example, pH 9-12. The sols are then added to a buffer, an acid, or a base to form an organosilicate solution having a pH of about 2 to about 12, preferably a pH of about 4 to about 10 and more preferably a pH of about 5 to about 9. For example, phenyltriethoxysilane (PTES) is hydrolyzed with an aqueous acid to form a phenylsilsesquioxane sol (PPSQ), which is combined with a silicate sol derived from a tetraethylorthosilicate and added to a buffer to form an organosilicate solution. The ratio of the organosilane to silicate precursor ranges from about 1:100 to about 10:1, more preferably, about 1:50 to about 2:1 and most preferably about 1:10 to about 1:1 on a molar basis.

For the purposes of the present invention, a biocomposite refers to a composite containing at least one biologically derived material. Biocomposites of the present invention include colloidal biocomposites and solid biocomposites. Colloidal biocomposites are an immediate product of the co-precipitation, and solid biocomposites are an isolated product from the colloidal biocomposites. A biocomposite is composed of two or more distinct materials having different physical characteristics and in which each material retains its identity while contributing desirable properties to the whole. A biocomposite is a mixture of two or more distinct biological materials that are closely associated with one another, but they are not necessarily covalently bound to each other.

In general, a biocomposite might be entirely homogenous where the constituent materials are mixed together on the molecular level. By "homogeneous" is meant that the distinct materials form a uniform structure or composition throughout the mixture. A biocomposite might also show some heterogeneity where the constituent materials partition into respective domains. These domains can range in size from nanometers to millimeters. A nanocomposite refers to a substantially homogenous composite where the domain sizes of the component materials are between 1 and 1000 nanometers in size. A definition of a nanocomposite can be found in Ajayan, P. M., *Nanocomposite Science and Technology (Wiley,* 2003). The biocomposite of the present invention is a nanocomposite of template molecules, biocatalysts, and silica or organosilicates.

The present invention provides a method for immobilizing biocatalysts, such as enzymes and cells. The method comprises the steps of: (a) mixing together a biocatalyst solution comprising one or more biocatalysts, a template solution comprising an organic template molecule, and a silicate solution, and (b) simultaneously precipitating the biocatalyst, silica and the organic template molecule to form a silica biocomposite, wherein the biocatalyst retains catalytic activity in the silica biocomposite. The pH of the mixture in step (a) is about 2 to about 12, preferably about 4 to about 10 and more preferably about 5 to about 9.

The ratio of protein/template molecule ranges from about 100:1 to about 1:100 on a mass basis, preferred protein/template ratios are from about 50:1 to about 1:50. More preferred template ratios are from about 10:1 to about 1:10.

The biocatalyst solution, the template solution and the silicate or organosilicate solution can be added in various orders; however, the order of addition may affect several parameters of the silica biocomposites formed, such as the loading and activity of the immobilized biocatalyst, and the porosity and particle size of the silica biocomposites. In one embodiment of the invention, the biocatalyst solution and the template solution are mixed first, and then the mixture is added to the silicate solution, resulting in an immediate formation of a colloidal silica biocomposite comprising the biocatalyst, the organic template molecule and the newly formed silicate matrix.

The rate of addition of the solution comprising the biocatalyst and the template molecule to the silicate solution can be varied. For example, the solution comprising the biocatalyst and the template molecule might be added slowly in a dropwise manner to the silicate solution. Alternately, the solution comprising the biocatalyst and the template molecule can be added to the silicate solution swiftly by pouring. The silicate solution can be stirred or otherwise agitated during the addition of the biocatalyst solution and the template solutions.

The addition of a biocatalyst, admixed with the organic template molecule, to the silicate solution results in the polymerization of the silicate monomers within a short period of time (e.g. seconds, minutes, or hours) to form a colloidal silica biocomposite comprising the template, silica or an organosilicate and the biocatalyst. The collidal silica biocomposite formed is subsequently isolated and recovered by various methods such as filtration, centrifugation, spray-drying, air-drying, freeze-drying, and settling, to form a solid silica biocomposite. The solid biocomposite is optionally washed to remove unbound material. The choice of isolation method influences the morphology and water content of the silica biocomposites so obtained, it may also affect the catalytic activity of the immobilized biocatalyst. For example, drying of the solid by lyophilization gives a fine, free flowing powder, whereas air-drying of silica biocomposites results in an agglomerated solid. Filtration is a preferred method of isolation of the said biocomposites from solution. Depth filters including pads of diatomatous earth and cheesecloth are especially preferred as a means of isolation of solid silica biocomposites.

The silicate or organosilicate solution used to immobilize biocatalysts in general has a silicate concentration between about 10 mM to about 1 M, usually about 100 mM to about 400 mM; and pH between about 5 to about 9. The silicate or the organosilicate solution prepared is usually mixed with the biocatalyst and template solution within about an hour, preferably within about 30 minutes, more preferably within about 10 minutes, or in any time frame selected, such that the silicate solution will not gel prior to being mixed with the biocatalyst and template solution.

In general, more than about 20% of the biocatalyst from the biocatalyst solution is immobilized and remains within the silica biocomposite. Preferably at least about 50%, more preferably at least about 80%, and most preferably at least about 90%, or even 100% of the total biocatalyst is present in the precipitated silica biocomposite.

The biocatalyst remains within the silica biocomposite even after several washing steps, including washes with salt solutions of high osmolarity (200 mM or more) and low pH (less than 5). The minimal loss of catalytic activity after washing of a protease-containing biocomposite is described in Example 3 of the present invention. Although prolonged washes or extreme high salt washes may cause a measurable loss of catalytic activity.

In general, the expressed or apparent specific activity of the immobilized biocatalyst differs from an equivalent amount of the free, unimmobilized biocatalyst. In some cases, typically those where biocatalyst activity is measured in water, the immobilized biocatalyst often has an expressed activity less than that of an equal amount of the free biocatalyst. In other instances, such as those where the biocatalyst activity is measured in a non-aqueous medium such as an organic solvent, the expressed specific activity of the immobilized biocatalyst is often significantly higher than that of the free biocatalyst (see Reetz, U.S. Pat. No. 5,817,493; and Reetz, et al. *Biotechnol. Bioeng.*, 49: 527-534 (1996)). It should be noted that the expressed activity of an immobilized enzyme results from a combination of several factors; the most important being the retained specific activity of the biocatalyst itself, in addition to the ability of the substrates to access the entrapped biocatalyst. The restricted ability of substrates to access the active site of immobilized enzymes is itself a function of many factors including the morphology and polarity of the matrix containing the biocatalyst, the fashion in which the biocatalyst assay is performed and the degree to which the substrate partitions into the matrix containing the biocatalyst.

When compared with an equivalent amount of a free, unimmobilized biocatalyst, an immobilized biocatalyst in silica biocomposite exhibits an expressed activity, relative to its substrate, of at least 0.1%. Preferably at least 1%, more preferably at least 10%, more preferably at least 50%, and most preferably at least 90% expressed activity is exhibited by the precipitated silica biocomposite.

It should also be noted that even where the expressed activity of an immobilized biocatalyst of silica biocomposite is low in comparison with the free biocatalyst, an immobilized biocatalyst still has several advantages over the free biocatalyst. Immobilized biocatalysts can be readily recovered and reused, in some cases multiple times. Immobilized biocatalysts can also be used in packed bed or fluidized bed reactors allowing continuous use. Immobilized biocatalysts can also be used under conditions that would otherwise rapidly denature the free unimmobilized biocatalyst. For these reasons, the benefits of immobilizing a given biocatalyst still exist even if the expressed specific activity is low relative to the free biocatalyst.

The present invention also provides a method of adding a solid material (filler) to the silicate solution prior to mixing with the biocatalyst and template solution. This solid material can be in the form of a particulate, a bead, a particle, a fiber or any other solid forms. The solid materials can be inorganic or organic materials, or a mixture of both. Examples of solid materials include rice hull ash, clay, diatomaceous earth, glass beads, starch granules, and the like. The silica biocomposite formed upon co-precipitation incorporates an amount of the filler material. The silica biocomposite formed may also be coated upon the filler material as in the case of larger beads or particles. The purpose of the filler is to provide for selected physical properties of the resulting silica biocomposite. Such properties include the size and morphology of the silica biocomposite particles, the ability to further process the material and its eventual mechanical attributes including hardness, expression of enzymatic activity and protein stability.

The present invention also provides a method of adding soluble additives to either the biocatalyst, the template solution, the silicate solution or mixtures thereof. Such soluble additives can be added prior to, during, or following the formation of silica biocomposites. These soluble additives are designed to influence the physical morphology of the biocomposites or the catalytic activity of the immobilized biocatalyst. Examples might include, but are not limited to, cross-linking reagents, surfactants, humectants, polymers, osmolytes, polyanions, nanoparticles, dyes, carbohydrates, chelating agents, antimicrobials, organosilanes, cofactors, allosteric activators, inhibitors, porogens that influence and/or increase the porosity of the composite, and the like.

The present invention provides silica biocomposites comprising catalytically active biocatalysts, silica or organosilicates and organic template molecules, wherein said silica biocomposite is substantially homogeneous unless a filler material is added. By substantially homogeneous, it is meant that the biocatalyst, silica and the organic template molecule are mixed together and form a uniform structure throughout the mixture; they are not partitioned into separate layers or domains, except where these domains measure less than 1000 nm in size. In one embodiment of the invention, the biocatalysts are enzymes. In another embodiment of the invention, the biocatalysts are whole cells or parts thereof. The morphology and other physical properties of the silica biocomposites of the present invention are varied through alteration of the template molecule, the silica precursors and the process conditions.

The silica biocomposite may contain one or more biocatalysts with distinct catalytic activities. Additionally, the silica biocomposite may contain associated cofactors and other small molecules required for catalytic activity. The silica biocomposite optionally contains filler materials, which increase the overall bulk volume.

One application of the silica biocomposites of the present invention is as immobilized biocatalysts such as immobilized enzymes. Immobilized biocatalysts are advantageous because in general biocatalysts are more stable and less prone to thermal and chemical inactivation in an immobilized form, as compared with the free biocatalysts in solution. Columns packed with immobilized biocatalysts can be used for continuous chemical transformation. Immobilized biocatalysts often exhibit altered properties relative to the free biocatalyst in solution. These differences include altered kinetic parameters, and changes in temperature and pH optima. Immobilized biocatalysts often possess greater operational stability relative to the soluble biocatalyst and in some cases can be used in a continuous mode for many months.

The silica biocomposites of the present invention are prepared by mixing the biocatalyst solution, the organic template solution and the silicate or organosilicate solution. The biocomposite produced comprises the biocatalysts, the template molecules and the silicate matrix. The structure of the biocomposite is influenced by the nature of each component, such as the template molecule, the protein, and the silica precursor, and the process of making the composite. For example, fast (several seconds or less) precipitation often results in small particles, and slow (seconds to minutes) precipitation often results in larger particles. The resulting composite materials obtained from this template directed process contain organic template and inorganic silicate polymer, thus they are often termed organic-inorganic hybrid materials. In general, the biocomposite of the present invention is an amorphous composite of aggregated nanoparticles and does not partition into layers.

In one embodiment of the invention, lipase-containing biocomposites (e.g. LIPOMAX™ and CAL-B) are used as biocatalysts for the production of fatty acid esters and other fine chemicals. Such composites can be used as suspensions in both aqueous and organic media, or in a continuous manner using a column packed with the composite materials.

Immobilized cellulases can be used in both textile treatment (depilling of cotton and stonewashing of denim fabric) and deinking of recycled paper. For these applications, immobilization of the enzyme prevents excessive degradation of the substrate commonly seen with soluble cellulases.

Immobilized glucose isomerase can be used as a catalyst for the production of high-fructose syrup from glucose. Immobilized lactase can be used for foodstuff modification, such as removing lactose from milk.

Immobilized proteases can be used for preventing microbial growth on surfaces or as mild skin exfoliating applications.

Immobilized glucose oxidase can be used as a reagent for glucose assays, for the removal of oxygen from foodstuffs, or for the production of gluconic acid and its salts.

Silica biocomposite comprising more than one enzymes that act in synergy provides corporative effects of the enzymes. The advantages of co-immobilizing enzymes that act in synergy are well known to those skilled in the art (see Balcao, et al. (2001) *Enzyme Microb Technol.,* 28:696-704 (2001) and Messing, *Biotechnology and Bioengineering,* 16: 897-908 (1974)). For Example, it is beneficial to co-immobilize catalase with glucose oxidase in silica biocomposite in order to prevent the accumulation of hydrogen peroxide.

Immobilized whole cells of *E. coli* JM109/pDTG601, which bear genes encoding for toluene dioxygenase, are useful for the dioxygenation aromatic compounds, used in fine chemical manufacture.

The following examples further illustrate the present invention. These examples are intended merely to be illustrative of the present invention and are not to be construed as being limiting.

EXAMPLES

Example A

General procedures for the immobilization of biocatalysts by co-precipitation with a silicate or organosilicate through the action of an organic template molecule.

A silicate sol is prepared through the acid hydrolysis of a tetraalkoxysilane, such as tetraethylorthosilicate (TEOS). An aliquot of the resulting silicate sol is added to either deionized water or a buffer such that the final concentration of the silicate is typically between 10 mM and 1 M, and the pH between 5 and 9. Alternately, a dilute (i.e. 1 M or less) sodium silicate solution is neutralized with an acid to give a silicate solution of concentration and pH as defined above. Such solutions should be used prior to the onset of gelation, a characteristic of the more concentrated silicate solutions, especially those at higher pH. The addition of an biocatalyst solution containing a template molecule, typically at 1-50 mg/mL, to the silicate solution results in the appearance of a white precipitate upon contact of the two solutions. The template molecule can be a low molecular weight (i.e. under 1 kDa) polyamine or a polypeptide. Polymers including polyethylenimine (PEI) and quaternized polyamine flocculants are also suitable. The silica biocomposites produced by this method are composed of a mixture of silica, the template molecule and the biocatalyst. The precipitate can be isolated by filtration or centrifugation and is then washed repeatedly with buffer and water. Finally, the material is dried in vacuo or in air and stored for later use. Enzyme assays are employed to determine the level of biocatalyst incorporation within the silica biocomposite, and the stability of the silica biocomposite upon exposure to various conditions.

The above general procedures are used to immobilize the following biocatalysts (Table 1):

TABLE 1

| Biocatalyst | Class | Organic template | Assay |
| --- | --- | --- | --- |
| BPN'Y217L | Protease | PEI, R5 silaffin peptide | Suc-AAPF-pNA hydrolysis |
| GG36 | Protease | Fluor-Ahx-R9 | Suc-AAPF-pNA hydrolysis |
| CALB | Lipase | PEI | pNP butyrate hydrolysis |
| Cutinase | Lipase | PEI, TA | pNP butyrate hydrolysis |
| Laccase | Oxidase | PEI, | ABTS oxidation |
| β-Glucosidase | Glycosidase | PEI, PPI | UBG hydrolysis |
| Acyl transferase | Esterase | PEI | pNP butyrate hydrolysis |
| Glucose isomerase | Ketoisomerase | PEI | Glucose isomerization |
| Glucose oxidase/catalase | Oxidase | PEI | Glucose oxidation |
| Lactase | β-galactosidase | PEI, PPI | ONPG hydrolysis |
| LIPOMAX ™ | Lipase | PEI, PPI dendrimer, TA | pNP caprate hydrolysis |
| E. coli JM109/pDTG601 | Microorganism | PEI | Toluene dioxygenation |

PEI = polyethylenimine,
TA = bis-(2-aminoethyl)-1,3-propanediamine,
PPI = polypropylenimine,
pNP = 4-nitrophenol,
UBG = Umbelliferyl-β-D-glucoside,
ONPG = o-nitrophenyl-β-D-galactoside.

Example 1

Preparation of a silica/PEI/protease biocomposite

The enzyme BPN'Y217L protease (a subtilisin variant) was incorporated into silica using the following procedures.

A silicate stock solution was prepared by mixing tetraethylorthosilicate (TEOS) (230 µL, 1 mmol), aqueous HCl (10 µL, 100 mM) and deionized water (760 µL) together with moderate agitation for 12 hours. An aliquot of this acid-hydrolyzed TEOS solution (100 µL) was then mixed with 25 mM Tris-HCl buffer (700 µL, pH 8.0) to give a buffered silicate solution.

A premixed solution containing 100 µL (10 mg/mL) polyethylenimine (PEI) in water and 100 µL (1 mg/mL) BPN'Y217L subtilisin was then added at once to the buffered silicate solution resulting in the immediate production of a white precipitate. The reaction appeared complete in less than 3 minutes. The mixture was then centrifuged at 14,000 g for 15 minutes, discarding supernatant. The precipitate was then vortexed with 1 mL deionized water, centrifuged again, and the precipitate frozen at −80° C. and lyophilized.

Example 2

GG36 with R5 silaffin template, TEOS sol

Gels and precipitates containing the R5 silaffin peptide (Kroger, N. et al., Science, 286: 1129-1132 (1999)) and the enzyme GG36 (a wild type subtilisin protease) in a silica biocomposite were prepared. GG36 subtilisin (2.3 mg, 64% w/w active protein) in Tris-Cl buffer (900 µL, 10 mM) at either pH 7 or pH 8 was prepared. Acid-hydrolyzed TEOS sol (100 µL of 1 M) was added to the buffered enzyme. Then R5 silaffin peptide (1.0 mg) was added and the mixture stirred overnight. The reaction mixture was centrifuged at 14000 rpm for 15 min. The supernatant was decanted and the solid washed twice with deionized water. The reaction performed at pH 7 resulted in a gel (smaller particles), and the reaction performed at pH 8 resulting in a precipitate (larger and denser particles). Without the R5 silaffin peptide, the subtilisin enzyme did not produce a precipitate.

Example 3

Enzyme assay of immobilized forms of BPN'Y217L protease

The protease/PEI/silica composites retained enzymatic activity shown by a standard colorimetric assay even after washes with brine and buffer solutions (Table 1). The substrate used was suc-AAPF-pNA (N-succinyl-Pro-Ala-Ala-Phep-nitroanilide) (Sigma) and the absorbance was measured at 410 nm as an indication of enzyme catalytic activity. The control used was BPN'Y217L protease adsorbed to silica 60 (Merck) and washed with purified water. Wash conditions (such as 200 mM NaCl) removed some protease from the control, but did not remove any enzyme from the silica biocomposite. The solid biocomposite shows catalytic activity towards the substrate; although the overall enzyme activity is lower than that of control. Importantly, the biocomposite remains active after two additional cycles involving recovery and washing of the solid material and subsequent enzyme assay (Table 2).

TABLE 2

Catalytic activity of protease biocomposites.

| Sample | 200 mM NaCl wash: supernatant activity | Purified water rinse: supernatant activity | Endpoint after 45 minutes (AU): Biocomposite activity |
| --- | --- | --- | --- |
| Fluorescein-Ahx-R9 + protease + silica | No catalytic activity, even overnight | No catalytic activity | 0.62 |
| PEI + protease + silica | No catalytic activity | No catalytic activity | 0.77 |
| Control: Silica 60 (Merck) with adsorbed protease | 0.114 AU/min. | 0.051 AU/min. | 1.66 |

Example 4

BPN'Y217L protease with PEI template, TEOS/PPSQ sol

An example that yields approximately 20 mg of a protease/organosilicate biocomposite is as follows.

A solution containing PEI (100 μL of 10 mg/mL) in water and BPN'Y217L protease solution (100 μL of 1 mg/mL) was premixed. In a separate polypropylene tube, a silicate solution was made with acid-hydrolyzed TEOS solution (100 μL of 1 M) and of a 50 mM sodium borate buffer (600 μL, pH 8.5). Separately, a solution of phenyltriethoxysilane (PTES) (241 μL, 1.0 mmol), aqueous HCl (234.5 μL of 60 mM), and ethanol (296 μL) was allowed to react for 2 hours to give a 1.3 M phenylsilsesquioxane sol (PPSQ).

The PPSQ sol (100 μL) and the PEI/protease organic solution (200 μL) were then added simultaneously to the buffered silicate sol for a total volume of 1 mL. Reaction immediately produced precipitate and appeared complete in less than 3 minutes. The reaction mixture was then centrifuged at 14,000 g for 15 minutes, discarding supernatant. The precipitate was then vortexed with 1 mL purified water, centrifuged again, and the precipitate frozen at −80° C. and lyophilized.

As with the silica/PEI/protease biocomposite, enzyme activity was measured at 410 nm using suc-AAPF-pNA as a substrate. A precipitate control containing PEI, PPSQ and silica did not catalyze substrate hydrolysis. The first wash of the protease biocomposite (made with PEI) did not contain any leached protein, with no substrate hydrolysis after 3 or more hours. All additional washes, including a 200 mM NaCl wash and a 20 mM MES buffer (2 mM $CaCl_2$, pH 5.5) also did not contain enzyme activity. The biocomposite showed efficacy in catalyzing substrate hydrolysis after repeated washes. A control precipitate made without PEI was catalytically active, but appeared to catalyze substrate hydrolysis at a lower rate than the protease biocomposite prepared with a PEI template.

Example 5

Immobilization of BPN'Y217L protease with an oligopeptide template in silicate/PPSQ A biocomposite of BPN'Y217L protease and silica was produced with the procedure detailed in Example 4 using 100 μL (10 mg/mL) fluorescein-Ahx-RRRRRRRRR peptide (R=arginine, Ahx=6-aminohexanoic acid) solution in place of 100 μL (10 mg/mL) PEI solution. The resulting fluorescent biocomposite was catalytically active against the suc-AAPF-pNA substrate.

Example 6

Immobilization of C. antarctica lipase B with PEI in silicate/PPSQ

This example yielded approximately 200 mg of a lipase/silica biocomposite.

A solution containing PEI (900 μL of 10 mg/mL) in water and CAL-B lipase solution (900 μL of 1 mg/mL active protein; 5 mg/mL total protein) was premixed in 100 mM sodium phosphate buffer (5.4 mL, pH 7.). In a separate polypropylene tube, a silicate solution was made, containing acid-hydrolyzed TEOS solution (900 μL of 1 M) and PPSQ sol solution (900 μL of 1.3 M). The enzyme solution (7.2 mL) was then added to the silicate solution (1.8 mL) for a total volume of 9 mL. A precipitate formed immediately upon contact of the two solutions and appeared to be complete in less than 2 minutes. The reaction mixture was then divided into ten 1 mL aliquots and centrifuged at 14,000 g for 15 minutes. The supernatant was discarded. For each aliquot, the precipitate was vortexed with 1 mL purified water, centrifuged again, removed, frozen at −80° C. and lyophilized.

Example 7

Immobilization of lactase with PEI and a phosphate buffered silicate sol (PBSi)

A stock solution of sodium silicate (14% NaOH, 27% $SiO_2$, Aldrich, Wis.) was diluted 10-fold with deionized water resulting in a final silicate concentration of approximately 0.62 M. An aliquot of this solution (4 mL) was mixed with 1 M phosphoric acid (1.1 mL) and deionized water (12.9 mL) giving a phosphate-buffered silicate (PBSi) solution of approximately pH 7.4. This solution was used within 20 minutes to avoid gelation. To this solution was added a premixed solution of lactase (Genencor, 1 mL of 410 ALU/mL), and polyethylenimine (1 mL of 20 mg/mL), which resulted in precipitation of a white solid material within seconds. The solid material was collected by centrifugation (8000 rpm, 10 min) and washed twice with deionized water.

The enzymatic assay of the material was determined using 2-nitrophenyl-β-D-galactoside (ONPG) as the substrate and monitoring the release of 2-nitrophenol at 410 nm. The immobilized lactase was found to have a specific activity of 57% relative to an equivalent amount of the free enzyme.

Example 8

Immobilization of cellulase/β-glucosidases by silicate coprecipitation

A 100 mM phosphate-buffered silicate (PBSi) solution was made by the addition of 1 M $H_3PO_4$ (4 mL) to ~0.62 M sodium silicate (8.8 mL) and deionized water (27.2 mL). This solution had a pH of about 5.5, and was used within 1 hour to avoid gelation of the solution. Three separate protein/polyamine solutions were made as in Table 3, and were added to the PBSi solution prior to its gelation.

TABLE 3

| Component | A | B | C |
| --- | --- | --- | --- |
| 2% polyethylenimine (PEI) | 500 uL | 700 uL | 900 uL |
| Cellulase (275 g/L, Genencor) | 500 uL | 300 uL | 100 uL |

Protein/polyamine mixtures A, B and C (0.5 mL) were added slowly in a dropwise manner (ca. 1 minute for complete addition) to 3 separate 100 mM PBSi solutions (4.5 mL) in 50 mL polypropylene conical tubes, which resulted in the immediate precipitation of a white solid. The mixture was vortexed thoroughly and then diluted with the addition of 5 mL of deionized water. The sample was centrifuged at 5000 rpm for 5 minutes, the supernatant decanted and the precipitate resuspended in deionized $H_2O$. This procedure was repeated twice. The resulting solid was dried in vacuo and assayed for β-glucosidase activity. The results are summarized in FIG. 1.

Example 9

Large Scale immobilization of cellulase/β-glucosidases by silicate coprecipitation A 100 mM phosphate-buffered silicate (PBSi) solution was made by the addition of 1 M $H_3PO_4$ (18 mL) to ~0.62M sodium silicate (39.6 mL) and deionized water (122.4 mL). This solution had a pH of about 5.5 and was used within 1 hour to avoid gelation of the solution. A protein/polyamine solution was made according to Table 4.

TABLE 4

| Component | Volume |
| --- | --- |
| 2% PEI | 10 mL |
| Cellulase (275 g/L) | 10 mL |

The protein/PEI mixture (20 mL) was added rapidly by pouring (ca. 1-2 seconds for complete addition) to the PBSi solution (180 mL) in a 500 mL polypropylene centrifuge bottle, resulting in the immediate precipitation of a white colloidal solid upon contact of the two solutions. Following thorough mixing of the solution, 200 mL of deionized water was added to dilute the sample that was then centrifuged at 5000 rpm for 5 minutes. The supernatant was decanted, and the remaining solid washed three times sequentially with deionized water. The resulting solid was dried in vacuo and assayed for β-glucosidase activity. Results are shown in FIG. 1.

The material made on the larger scale by rapid addition of the protein/polyamine mixture to the PBSi sol was approximately threefold more active with respect to enzyme activity.

Example 10

Immobilization of LIPOMAX™ lipase

LIPOMAX™ lipase (P. alcaligenes lipase, Genencor) (9 mg) was added to 50 mM Tris-Cl (5 ml, pH 8) and 2% PEI solution (5 mL). This solution was then added with stirring over 2-3 seconds to a premixed PBSi solution consisting of deionized water (66.2 mL), sodium silicate (19.8 mL of about 0.62 M made by 1/10 dilution of commercial sodium silicate solution from Aldrich), and 1 M phosphoric acid (9 mL). A white colloidal solid was formed immediately upon addition of the two solutions. The mixture was subsequently diluted with deionized water (100 mL) and centrifuged for 5 min at 5000 g. The solid pellet was then washed three times with (100 mL) and resuspended in deionized water (25 mL). Drying of the composite under vacuum or at atmospheric pressure gave a fine, white powder containing catalytically active LIPOMAX™ lipase.

A modified procedure to that described above involved the addition of gluteraldehyde, a cross-linking reagent (1% final v/v), to the LIPOMAX™/PEI solution in order to increase the immobilization yield of the enzyme. The LIPOMAX™/PEI/ gluteraldehyde solution was than added to PBSi and the resulting precipitate isolated, washed and dried as describe above.

As a control, a solution of LIPOMAX™ enzyme (9 mg) in 50 mM Tris-Cl (5 mL, pH 8) was precipitated with ammonium sulfate (2.75 g) in 100 mM sodium phosphate (5 mL, pH 7, 55% ammonium sulfate w/v) and then crosslinked by the addition of glutaraldehyde (400 μL of 25%). This was incubated on a shaker overnight at 4° C. to produce cross-linked enzyme aggregates (CLEA) (described by Cao, *Org. Lett.* 2(10): 1361-1364). Deionized water (10 mL) was added and the enzyme harvested by centrifugation at 5000 g for 15 min. The enzyme was then washed 3 times with deionized water (10 mL) and resuspended in deionized water to a final volume of 10 mL.

Immobilization yields and the specific activity of the biocomposites produced are summarized in Tables 5 and 6. Despite the incomplete incorporation of the lipase into the PEI/silica biocomposite, the catalytic activity of this material exceeded that of the other two preparations as determined by the release of p-nitrophenol (pNP) from pNP caprate as determined by the absorbance reading at 410 nm. This example demonstrates the improved expressed activity of a LIPOMAX™ silica biocomposite relative to a commonly employed method for enzyme immobilization, namely the CLEA technique.

TABLE 5

Enzyme immobilization yield as determined by Bradford assay.

| Immobilization method | % incorporation of added protein |
| --- | --- |
| PEI/silica | 44% |
| PEI/Glut/silica | 96% |
| CLEA | >90% |

TABLE 6

Lipase activity as determined by absorbance at 410 nm.

| Immobilization method | Initial | Wash 1 | Wash 2 | Wash 3 | Final |
| --- | --- | --- | --- | --- | --- |
| PEI/silica | 1.35 | ND | ND | ND | 1.39 |
| PEI/Glut/silica | 0.364 | ND | ND | ND | 1.016 |
| CLEA | 0.494 | ND | ND | ND | 0.204 |

PEI/silica=LIPOMAX™/PEI/silica composite (Si-LIPOMAX™) PEV/Glut/silica =LIPOMAX™/PEI/silica/gluteraldehyde composite CLEA=LIPOMAX™ cross-linked enzyme aggregate.

Example 11

Thermal activity of different immobilized forms of LIPOMAX™ lipase

Figure 2:
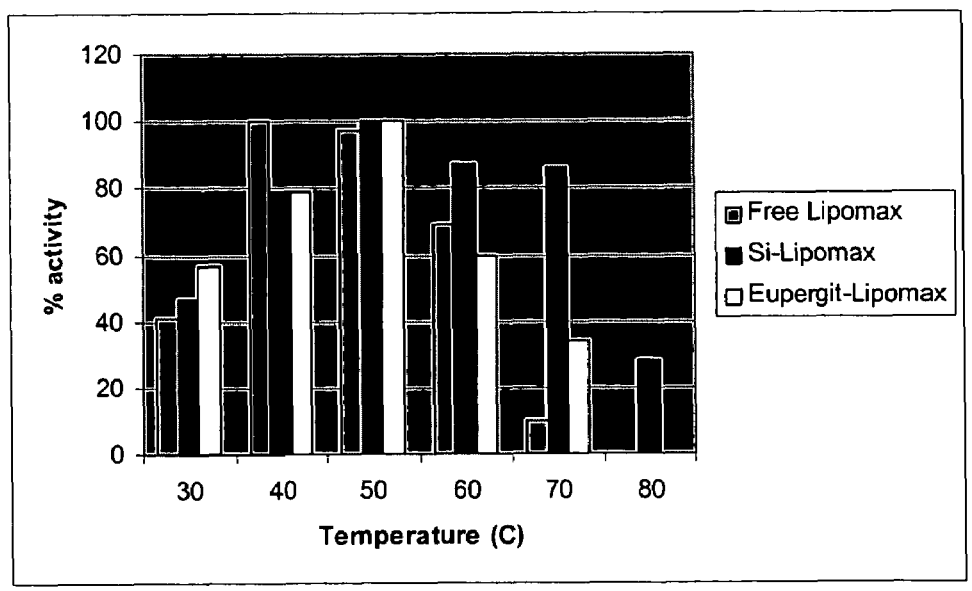
FIG. 2 depicts the thermal activity of LIPOMAX™ a lipase in both free and immobilized forms (silica biocomposite and EUPERGIT® C beads).

The relative thermal activity of various forms of LIPOMAX™ lipase was determined between 30° and 80° C. Thermal activity refers to the activity of an enzyme as a function of temperature. The enzyme was added to pre-heated buffer in a temperature-controlled Uv-spec and the reaction was initiated by the addition of 1 mM pNP-caprate. The activity was monitored at 410 nm by the release of pNP. A comparison was made between the soluble (free) enzyme and the enzyme immobilized on EUPERGIT® C beads (Sigma) and immobilized via the PEI-coprecipitation process (Si-LIPOMAX™, see Example 10). FIG. 2 summarizes the results. The Si-LIPOMAX™ was significantly more active than the other forms at 60° and 70° C. In addition, the Si-LIPOMAX™ retained 25% activity at 80° C. in contrast to the other two forms, which are inactive at this temperature.

Example 12

Synthesis of Heptyl Oleate

For a comparative study, free and immobilized forms of LIPOMAX™ were used for the esterification of oleic acid and heptanol in isooctane. The immobilized forms used were lyophilized LIPOMAX™, LIPOMAX™ lyophilized in the presence of KCl, LIPOMAX™ immobilized on ELPERGIT® C beads, and LIPOMAX™ granules (Genencor, Calif.), to catalyze the formation of heptyl oleate. The reactions (5 ml) contained 10 mg of enzyme, 50 mM oleic acid and 50 mM heptanol. The reactions were carried out at 50° C. over 55 hrs with stirring. Aliquots (100 µL) of the reaction mixture were withdrawn periodically (at 0, 2, 6.5, 23.5, 30, 48 and 54.5 hours) from the reaction mixture and clarified by centrifugation (14,000 g for 5 minutes). A portion of the supernatant (25 µL) was then diluted into ethyl acetate (1 mL) and analyzed for heptyl oleate by GC/MS.

An Agilent 6890 GC/MS was used for the analysis with a split injector held at 200° C. and run at a split ratio of 50:1 in ramped flow mode, interfaced into an HP-5MS capillary column (0.25mm×30 m×250 µm, Agilent, Calif.). Injection volume was 1 µL. Helium was the carrier gas, the initial flow rate was 1 mL/min, held for 4 minutes, increasing to 2 mL/min over 4 minutes and then to 3 mL/min over 2 minutes for a total run time of 10 minutes. The oven program began at 120° C. increasing to 220° C. over 4 minutes and then to 300° C. over 4 minutes, followed by a 2-minute hold. Quantitation of the heptyl oleate peak was performed by integration of the ion corresponding to m/z 83.

Figure 3:
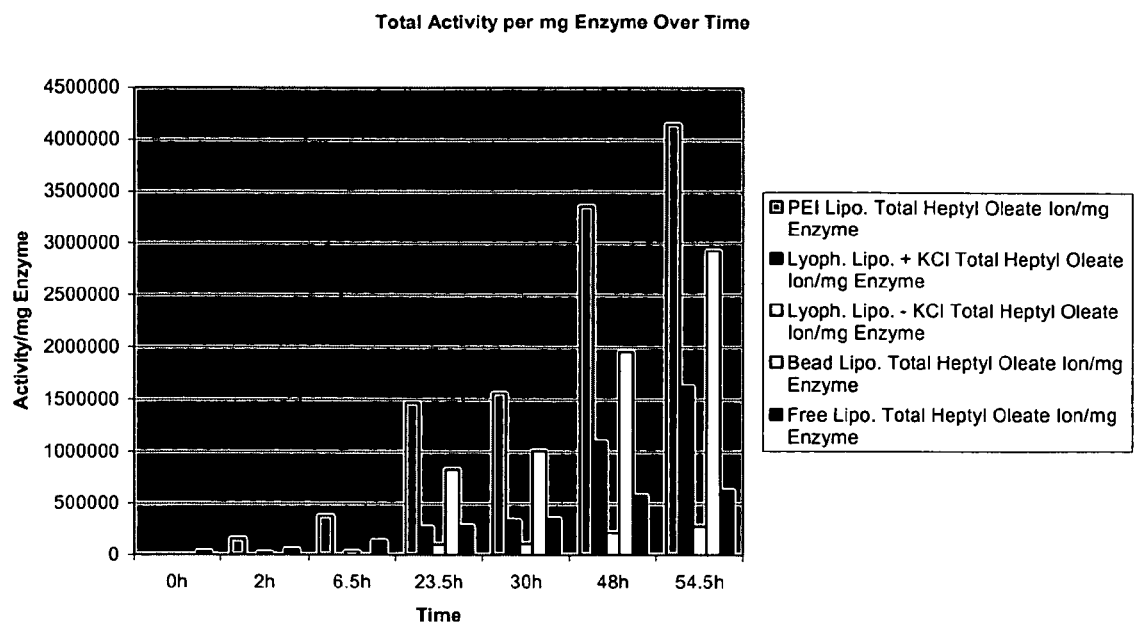
FIG. 3 depicts the relative extent of synthesis of heptyl oleate with different forms of LIPOMAX™ in iso-octane at different time points.

The relative rates of heptyl oleate synthesis by different forms of LIPOMAX™ lipase at different time points are shown in FIG. 3. The LIPOMAX™ silica biocomposite is superior to the other forms giving both the highest rate and extent of heptyl oleate synthesis.

Example 13

Immobilization of Glucose Isomerase

Glucose isomerase concentrate (Gensweet™, 0.5 mL, Genencor) was mixed with 2% PEI solution (2.5 mL) and water (2 mL). This solution was added swiftly by pouring (about 1-2 seconds for complete addition) to a sodium phosphate/silicate buffer (100 mM phosphate, 200 mM silicate, pH 8) resulting in the formation of a white, colloidal solid upon contact of the two solutions. Water (20 mL) was added and the solid material collected by centrifuged at 5000 g for 5 minutes. The supernatant was decanted and the pellet resuspended in 100 mM phosphate buffer (25 mL pH 7.4). Assay of the supernatant revealed only 10% unbound protein, the other 90% being immobilized in the silica biocomposite. Assay of the solid demonstrated the ability to convert glucose to fructose as determined by HPLC using a Bio-Rad AMINEX® HPX-87C HPLC column (Bio-Rad, CA) eluted with deionized water coupled with refractive index (RI) detection.

Example 14

Production of cis-1,2-dihydronaphthalene diol by immobilized whole cells of E. coli JM109/DTG601

Toluene dioxygenase is a versatile, broad specificity enzyme that has been used for the production of a variety of chiral cis-dihydrodiols derived from the corresponding aromatic compounds (Hudlicky, T. et al., *Aldrichimica Acta*, 32:35-62). This multisubunit enzyme catalyzes an energy requiring reaction that is dependant on a source of reduced pyridine nucleotide. As such it is most often used as a whole cell biocatalyst. One such organism, which has been used extensively for the production of cis-dihydrodiols, is E. coli strain JM109/DTG601. This strain was grown in L-broth aerated on a rotary shaker at 200 rpm at 37° C. to an OD of 0.6 measured at 600 nm. Enzyme production was induced by the addition of isopropyl-beta-D-thiogalactopyranoside, 100 µM. The cells were further cultured, as above, to an OD of 2 measured at 600 nm. The grown cells were collected by centrifugation at 10,000 g for 10 minutes and were washed with sodium phosphate buffer (100 mM, pH 7.4). The cells were resuspended in a volume of buffer 3 times the wet weight. An aliquot of the cell suspension (0.4 mL) was mixed with a solution of 2% PEI (0.4 mL) and mixed thoroughly. In a separate polypropylene vessel a 1 M phosphoric acid solution (1 mL) was mixed with deionized water (5.5 mL) and a sodium silicate solution (3.5 ml of 0.62 M) to give a phosphate buffered silicate solution (PBSi) with a pH of 7.

The mixture of E. coli cells and PEI (0.8 mL total volume) is than added at once to the PBSi solution resulting in the immediate formation of a white, colloidal solid. This solid was collected by centrifugation (5,000 X g, 5 minutes) and the supernatant decanted. The solid pellet was resuspended and washed in 100 mM sodium phosphate. buffer (pH 7.4) followed by centrifugation. This washing process was repeated to give a silica biocomposite containing immobilized E. coli JM109/DTG601 cells as wet slurry. A portion of this material was lyophilized resulting in a tan-colored free-flowing powder. A control comprising lyophilized unimmobilized cells was also prepared.

Figure 4:
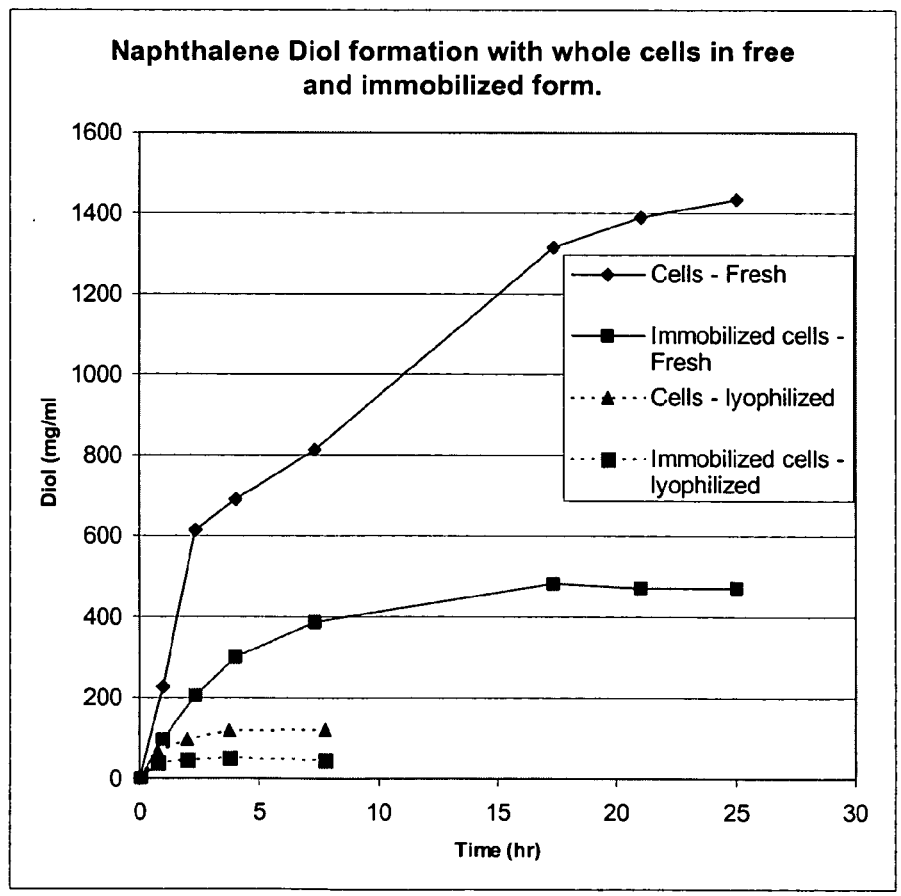
FIG. 4 depicts the rate of conversion of toluene to a cis-diol derivative by *E. coli* JM109/DTG601 cells in both free and immobilized form.

The silica biocomposite prepared above was examined for its ability to catalyze the dioxygenation of naphthalene to the corresponding cis-1,2-dihydrodiol. Each reaction contained in 50 mL; 200 mM $KPO_4$, pH 7, 0.2% glucose, 15 mg naphthalene (finely ground), and 400 µL of resuspended free cells or the amount of biocomposite containing the equilivant amout of cells. The reactions were placed in 250 mL flasks and incubated on a rotory shaker at 200 rpm at 37° C. Samples were taken at indicated intervals, centrifuged to remove cells or biocomposite, and the concentration of naphthalene-cis-1, 2-dihydrodiol determined by UV spectroscopy ($E_{M,262nm}$=8, 580). The results, depicted in FIG. 4, confirm that the immobilized E. Coli JM109/DTG601 cells retain catalytic activity. The catalytic activity of the freshly immobilized cells was around 30% relative to an equivalent amount of fresh, unimmobilized cells. Lyophilization of both the immobilized and free cells resulted in catalytic activities of under 10% relative to the fresh, unimmobilized cells.

Although the invention has been described with reference to the presently preferred embodiments, it should be understood that various modifications could be made without departing from the scope of the invention.

What is Claimed is:

1. A biocomposite comprising co-precipitates prepared by the steps of:
   (i) obtaining a buffered silicate solution comprising alkali metal silicate or an alkyl siliconate salt and having a pH about 5 to about 9,
   ii) mixing together (a) an enzyme solution comprising one or more enzymes, (b) the buffered silicate solution, and (c) a polyamine or a modified polyamine solution,
   (iii) simultaneously precipitating the enzymes, the alkali metal silicate or the alkyl siliconate salt, and the polyamine or the modified polyamine from the mixture of the solutions to form a precipitate and a supernatant, and
   (iv) removing the supernatant and recovering the precipitate to obtain a biocomposite,
   wherein said biocomposite retains at least 80% of the enzymes from the initial enzyme solution, and the enzymes in the biocomposite retain at least 50% of the catalytic activities in comparison with that of the initial enzyme solution.

2. The biocomposite according to claim 1, wherein said biocomposite is colloidal or solid.

3. The biocomposite according to claim 1, further comprising one or more cofactors or small molecules required for biocatalytic activity.

4. The biocomposite according to claim 1, wherein said enzyme is a protease, a lipase, a glycosidase, an oxidoreductase, an oxidase, a ketoisomerase, or an esterase.

5. The method according to claim 4, wherein said protease is a subtilisin.

6. The method according to claim 1, wherein said one or more enzymes are catalase and glucose oxidase.

7. The biocomposite according to claim 1, wherein said polyamine or said modified polyamine is linear or branched polyethylenimine, linear or branched polypropylenimine, polyallylamine, or polyvinylamine.

8. The biocomposite according to claim 1, wherein said polyamine or said modified polyamine is an amine selected from the group consisting of spermidine, spermine, triethylenetetramine, and bis(2-ethylamino)- 1,3 -propanediamine.

9. The biocomposite according to claim 1, wherein said modified polyamine is a fluorophore-modified polyamine.

10. The biocomposite according to claim 1, further comprising one or more filler materials.

11. The biocomposite according to claim 1, wherein said alkali metal silicate is sodium silicate, potassium silicate, or cesium silicate.

12. The biocomposite according to claim 1, wherein said alkyl siliconate salt is sodium alkyl siliconate, potassium alkyl siliconate, or cesium alkyl siliconate.

13. The biocomposite according to claim 12, wherein said alkyl siliconate salt is sodium methyl siliconate.

14. The biocomposite according to claim 1, wherein in step (ii), the enzyme solution and the polyamine or a modified polyamine solution are pre-mixed before mixing with the buffered silicated solution.

* * * * *

UNITED STATES PATENT AND TRADEMARK OFFICE
CERTIFICATE OF CORRECTION

PATENT NO. : 7,642,077 B2
APPLICATION NO. : 11/007437
DATED : January 5, 2010
INVENTOR(S) : Bond et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 383 days.

Signed and Sealed this

Sixteenth Day of November, 2010

David J. Kappos
*Director of the United States Patent and Trademark Office*

SEQUENCE LISTING

```
<160> NUMBER OF SEQ ID NOS: 2

<210> SEQ ID NO 1
<211> LENGTH: 19
<212> TYPE: PRT
<213> ORGANISM: Artificial Sequence
<220> FEATURE:
<223> OTHER INFORMATION: R5 silaffin peptide
```

```
-continued

<400> SEQUENCE: 1

Ser Ser Lys Lys Ser Gly Ser Tyr Ser Gly Ser Lys Gly Ser Lys Arg
1               5                   10                  15

Arg Ile Leu

<210> SEQ ID NO 2
<211> LENGTH: 9
<212> TYPE: PRT
<213> ORGANISM: Artificial Sequence
<220> FEATURE:
<223> OTHER INFORMATION: arginine oligomer

<400> SEQUENCE: 2

Arg Arg Arg Arg Arg Arg Arg Arg Arg
1               5
```